(12) United States Patent
Delhom Munoz et al.

(10) Patent No.: US 9,579,190 B2
(45) Date of Patent: Feb. 28, 2017

(54) IMPLANTATION DEVICE FOR INTRASTROMAL PROSTHESES

(75) Inventors: Salvador Gabriel Delhom Munoz, Parque Tecnologico (ES); Pere Manel Del Campo Garcia, Parque Tecnologico (ES); Rafael Ignacio Barraquer Compte, Parque Tecnologico (ES)

(73) Assignee: IMEX CLINIC, S.L., Paterna (Valencia) (ES)

( * ) Notice: Subject to any disclaimer, the term of this patent is extended or adjusted under 35 U.S.C. 154(b) by 529 days.

(21) Appl. No.: 14/119,728

(22) PCT Filed: May 25, 2012

(86) PCT No.: PCT/ES2012/070381
§ 371 (c)(1),
(2), (4) Date: Nov. 22, 2013

(87) PCT Pub. No.: WO2012/160236
PCT Pub. Date: Nov. 29, 2012

(65) Prior Publication Data
US 2014/0094907 A1    Apr. 3, 2014

(30) Foreign Application Priority Data

May 26, 2011   (ES) .................................. 201130860

(51) Int. Cl.
*A61F 2/14*    (2006.01)
(52) U.S. Cl.
CPC .............. *A61F 2/148* (2013.01); *A61F 2/147* (2013.01)

(58) Field of Classification Search
CPC .. A61F 9/013; A61F 9/001; A61F 2/14; A61F 2/147; A61F 2/148; A61F 9/0026; A61F 9/0008; A61F 2/145
(Continued)

(56) References Cited

U.S. PATENT DOCUMENTS

| 4,452,235 A | 6/1984 | Reynolds |
| 4,671,276 A | 6/1987 | Reynolds |

(Continued)

FOREIGN PATENT DOCUMENTS

| EP | 0 636 011 | 2/1995 |
| ES | 2160599 | 11/2001 |
| WO | 99/63912 | 12/1999 |

*Primary Examiner* — Kathleen Holwerda
*Assistant Examiner* — Socrates L Boutsikaris
(74) *Attorney, Agent, or Firm* — Greenblum & Bernstein, P.L.C.

(57) ABSTRACT

Implanting device for intrastromal prosthesis that introduces segment (ring) onto inside of intrastromal tunnel in a patient's cornea. Device includes a ring holder having clamp to support segment to be inserted and a cylinder base having hollow cylindrical shape and first and second cylinder ends. Rotatable impeller tip device, including an impeller tip arm and impeller tip, is joined to first cylinder end and over ring holder, a protective element arranged to protect clamp that is positionable over rotatable impeller tip device, and a block cover, arranged on second cylinder end. A rod, projecting from block cover and into cylinder base has a free end with a recess that separates a first wall configured to concurrently move clamp and impeller tip arm in a first direction and a second wall configured to move clamp relative to impeller tip arm in a second direction opposite first direction.

9 Claims, 5 Drawing Sheets (58) Field of Classification Search
 USPC .................. 606/107, 166; 623/5.12, 5.11
 See application file for complete search history.

(56) References Cited

U.S. PATENT DOCUMENTS

| | | |
|---|---|---|
| 4,766,895 A | 8/1988 | Reynolds |
| 4,961,744 A | 10/1990 | Kilmer et al. |
| 5,188,125 A | 2/1993 | Kilmer et al. |
| 5,312,424 A | 5/1994 | Kilmer et al. |
| 5,403,335 A | 4/1995 | Loomas et al. |
| 5,505,722 A | 4/1996 | Kilmer et al. |
| 5,792,161 A | 8/1998 | de Almeida Cunha |
| 6,051,023 A | 4/2000 | Kilmer et al. |
| 6,565,584 B1 | 5/2003 | Mathis et al. |
| 6,602,266 B1 | 8/2003 | Loomas et al. |
| 6,632,232 B1 | 10/2003 | Loomas et al. |
| 2004/0249403 A1 | 12/2004 | Loomas et al. |

IMPLANTATION DEVICE FOR INTRASTROMAL PROSTHESES

CROSS-REFERENCE TO RELATED APPLICATIONS

This application is a U.S. National Stage of International Application No. PCT/ES2012/070381 filed May 25, 2012, which claims priority of Spanish Application No. P 201130860 filed May 26, 2011.

OBJECT OF THE INVENTION

The present invention, which is directed to an implanting device for an intrastromal prosthesis has essential new characteristics and significant advantages over current methods to achieve the same goals available through existing technology.

More specifically, the invention offers a disposable device especially conceived and designed to introduce a segment or ring onto the inside of the intrastromal tunnel effected in the patient's cornea with the aid of a femtosecond laser, without requiring forceps and with the aid of an injector-clamp connected to a ring-holder equipped for coupling to the end of a cylinder base or tunnel. The introducer is itself envisaged as a one-piece rotatable impeller tip device, referred to by the inventors as a "Delhom apparatus" coupleable to the ring holder that is furnished with an impeller thrust tip, and a block cover coupling to the opposite end of the cylinder base and from which an extension rod projects longitudinally, that is furnished with a recess on the free end and additionally finishes in an anchor point configured to be introduced into an end groove of the intrastromal segment. The end of the assembly opposite to the coupling of the block cover, admits the incorporation of a protective clamp, aimed directly at the Delhom apparatus discussed above.

This invention falls within the industrial sector application field dedicated in particular to the manufacture of prostheses for the treatment of keratoconus of the cornea.

Backgrounds

Experts in the area are familiar with the large number of people who are affected by a cornea pathology known as keratoconus. The term "keratoconus" is derived from two Greek terms "kerato" (cornea) and "konos" (cone). It is a condition in which the normal shape of the cornea is distorted and develops a deformation in the shape of a cone that changes and progressively alters the patient's vision, making it ever more blurry. The disease process depends on the age of the patient and the onset of symptoms. Normally, the younger the patient and more precipitous the onset of keratoconus symptoms occurs, the more rapid the progress; it always presents bilaterally and asymmetrically, either owing to congenital alterations or provoked through weakness in the corneal tissue (corneal surgery or previous trauma).

In the present day different treatment modalities are known, depending on the degree and corneal deformation process, these are listed here below:
  glasses in the early stages
  contact lenses if glasses are no longer effective
  intracorneal rings when the eye develops an intolerance for contact lenses and there is evidence of disease progression
  Cross-linking, or ultraviolet light treatment to halt the progress of keratoconus corneal transplant in more advanced stages of keratoconus and in cases where other options do not offer any hope of improvement (for example, corneal scarring, and very advanced keratoconus).

Exactly as has been shown, in the early stages the patient can use glasses.

Nevertheless, when the disease progresses, the narrowing and deformation of the cornea causes a high irregular stigmatism that cannot be treated with glasses. In these cases it is important to use hard contact lenses that improve vision even if they do not halt the progression of the keratoconus, making surgery the only option for stopping the progressive deformation of the cornea. Cross linking treatment is effective in stopping the evolution of keratoconus, can still be used in cases where there is good corneal thickness.

In light of this, determined implantable prostheses have been developed to be used in those cases where the disease has progressed to the point where the treatments discussed earlier are effective; these prostheses achieve many more practical outcomes for the patient. These prostheses consist of longitudinal segments in an arc configuration that are implanted by using intrastromal tunnels both to guide the segments and for those that are affixed. These tunnels vary as much in width as in internal and external diameter, depending on the characteristics of the prosthesis.

At present, four design types of implants are used:
  triangular section segments: a section in the form of an isosceles triangle with different arc longitudes and thicknesses;
  trapezoid section segments: a section in the form of a triangle truncated at the top;
  hexagonal section segments: a section with six corners; and
  oval section segments: a transverse section with oval configuration.

In all cases the previously mentioned segments that use current techniques, longitudinal arched bodies have openings that facilitate the insertion of a segment inside the corneal tunnel by use of a Sinskey hook. The elasticity of corneal tissue tends to cause problems with segment implantation. Additionally, segment manufacture uses milling and the material used is PMMA (polymethacrylate), without external buffing which means that the quality of the finished product is determined by the wear of the diamond tool that is used.

All this, together with the limitations of the software used in manufacture, makes the mechanization of the segment difficult, some of which are the following:
  fractures during handling;
  deposit of materials on the inside of the hole and consequent infection risk;
  Necessity of using Sinskey hooks: risk of intrastromally scratching the bed of the tunnel thereby causing infections;
  poor angulation to ease the implantation of the segment.
  Milling of PPMA:
  The excessive use of the diamond produces poor finished
    products with risks of fracture or deposits with consequent infection risks.
  Software Limitations:
  Impossibility of using free software that permits the production of all segments desired.

There are two established techniques for manufacturing intrastromal tunnels: manual and femtosecond laser. Manual technique employs various instrumental tunnelling materials manufactured in titanium and a diamond knife. The tunnelling instruments do not so much cut as they delaminate intrastromally to create a tunnel, which incurs a high risk of perforation and in some cases requires the use of a suction console to keep the eye in a fixed position while the tunnel is being created. Complications that can arise with the manual technique are wide incisions, infections, tunnel asymmetry, deposits in the tunnel and post-operative trauma, among others.

In the case of femtosecond laser techniques, the laser provides pulses of intrastromal energy that causes a separation of the lamellae and creates a tunnel and the prosthesis entry incision. This technique provides several advantages over the manual technique since it is more sterile, less traumatic, provides exact depth without diameter limitation and less post-operative trauma among others.

For segment insertion, forceps are customarily used, which usually includes notches to ensure that the segment does not "gap" or jump, thereby getting lost. In practice, the implantation of the segments by known methods presents the usual difficulties and disadvantages such as the fact that the segments tend to jump or are lost, or are shattered by tweezers and are otherwise difficult to adjust, with the added difficulty that the segments can be manufactured with different sections and parameters which gives rise to the possibility that the tweezers may not grasp the segment adequately.

When the possibilities offered by existing technology as covered in this brief commentary are taken into account, and the characteristics identified with each one, the present invention has as its primary objective the development and creation of an intrastromal segment for implantation in intrastromal tissue, concretely in the patient's cornea, through exclusive application of laser technology that allows us to eliminate at least a good part of the inconveniences and disadvantages that have been outlined above, and which uses a surgery that is the least traumatic possible, and with the least possible risk of causing complications. This goal is fully realized in the intrastromal segment that will be the described in what follows.

In particular, the device proposed by the invention is designed in such a way that the necessity of using tweezers is avoided, since it is naturally disposable, easy to use, and defined by the following characteristics:

it incorporates an injector/clamp with micro-marks designed to join the grooves of the segment;

it is disposable and is prepared with the segment so that it will not jump or implant itself incorrectly;

it is universal with respect to its use, that is to say it can be adapted to any segment independent of its dimensions with respect to the longitude of the arch, the thickness, the width, . . . , etc.;

it aids the insertion operation while also eliminating the risks associated with the former instrumental.

For all that, the insertion device has been conceived of as a circular cross-section, cylindrically shaped, adaptable for manufacture from diverse materials, such as titanium or plastic as is suitable, prepared to join to the ring carrier equipped with a guide track that holds the segment to be implanted. This piece constitutes the cylindrical base or tunnel, which is adapted to be joined by its bottom end to a unit equipped with a ring holder configured as a guide track in which the segment is located for insertion. The ring couples to the Delhom apparatus furnished with an impeller tip projecting such that when the assembly is loaded it remains situated in the inside of the guide track of the ring-holder against the end of the thrust of the segment (also identified as a ring for descriptive purposes), the assembly protected by a protective clamp configured as a shield covering to close the introducer at this end, and dimensioned to couple to the Delhom apparatus, being the protective clamping piece furnished with a central window to provide an inferior perspective and sterilization, and a window extending toward the side wall to verify the loaded assembly. On the opposite end the cylinder base or tube is closed with a block cover from which it extends a rod longitudinally positioned on the inside of the cylinder corridor along the assembly, with a recess on its free end for positioning the top portion of the carrier arm of the ring-holder and the impeller tip of the Delhom apparatus ending in an anchor point sized for insertion into an end groove, and the segment or ring portals. The block cover includes an axial opening for sterilization and an upper view of the assembly.

In such conditions the segment or ring can be inserted into the intrastromal tunnel by pushing on the back end in the direction of the insertion, and after the removal of the assembly while the segment holds its position forming a ceiling with the impeller tip; subsequently this piece can be removed leaving the segment inserted on the inside of the corneal tunnel.

According to the preceding discussion, the introducer is, in its disposable housing, as it has been conceived of by the invention. Nevertheless, alternatively, the insertion device admits a variation in which the cylinder base or tube, optimally of titanium, is recoverable. This version uses the same elements already mentioned by the first version but the carrier device of the ring holder is made in such a way that it constitutes the base over which the corresponding Delhom apparatus is manipulated with the goal of positioning the segment or ring in its place.

BRIEF DESCRIPTION OF THE DRAWINGS

These and other features and advantages of the invention will be made more clear in the detailed description that follows an example of the preferred method of insertion provided solely by illustration and not limited, with reference to the accompanying illustrations, in which.

DETAILED DESCRIPTION OF PREFERRED EMBODIMENT

Figure 1:
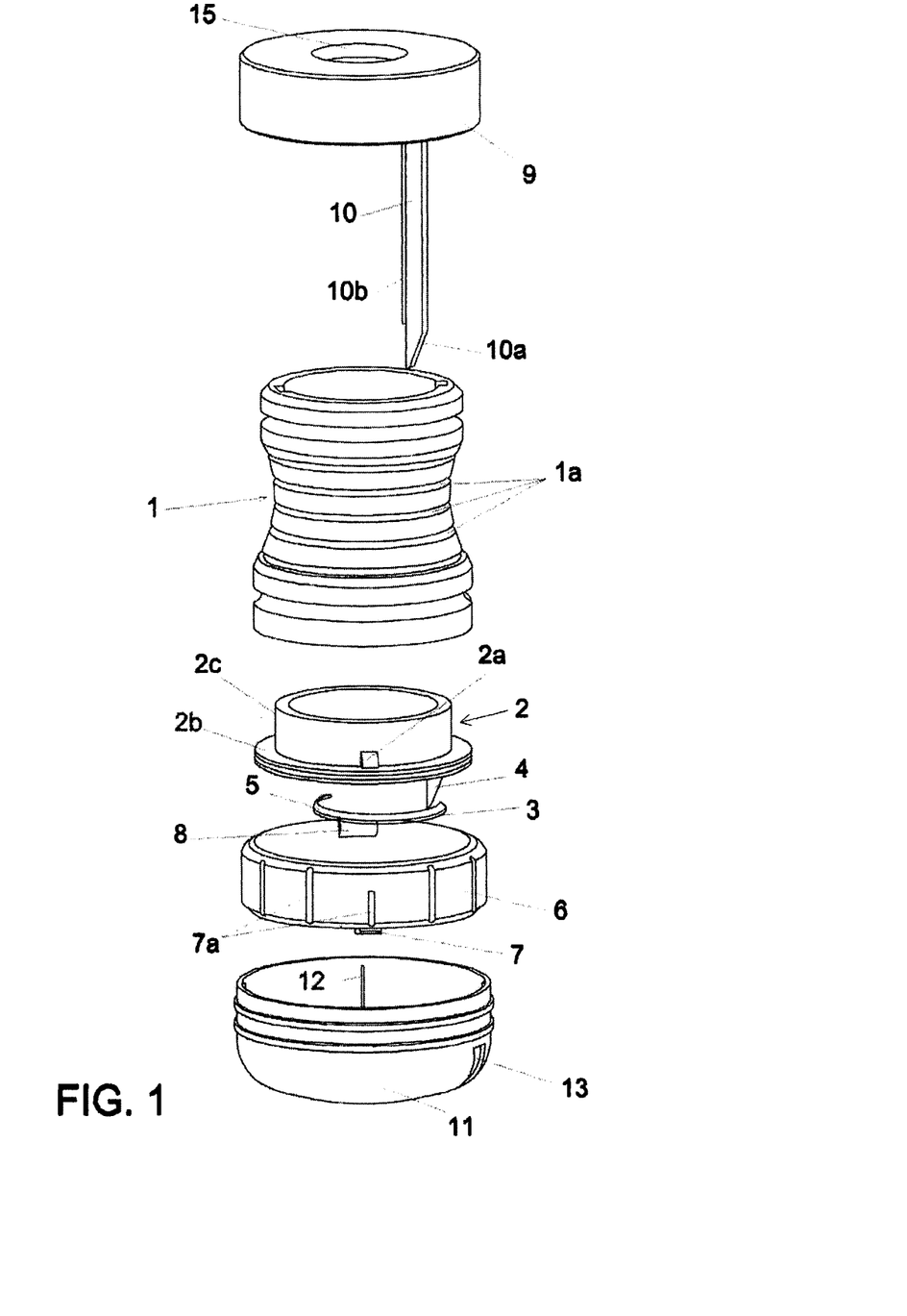
FIG. 1 schematic view of a cross section in perspective of the introducing device for intrastromal prosthesis as described in the invention.

Only and exactly as it has been discussed in the preceding, the detailed description of the template for preferred implementation of the invention object shall be carried out in the following with the aid of annexed drawings, in which identical numerical references shall be used to designate the corresponding parts of their equivalents. Thus, turning our attention in the first place to the representation that appears in FIG. 1 of the drawings, one can discern a schematic view in perspective of a cross section of the introducing device for intrastromal segment or ring as described in the invention. In agreement with the representation, the introducer is built on a cylinder base or tube (1), cylindrically shaped, made of titanium or plastic as conditions dictate, hollow inside and furnished with a multitude of perimeter striations to facilitate the secure attachment of the piece. This cylinder base 1 is made to couple on one of its ends to piece (ring holder) (2) which includes a cylinder shaped and hollow body (2c), which extends from a perimeter skirting (2b) that forms an insertion ceiling of cylindrical body (2c) on the inside of the cylinder base or tube 1, and that makes up a ring holder, such that a clamp (3 of a segment or ring (5) to be inserted is connected. The clamp (3) joins to an arm (4) projected outwardly from the piece (2) so that clamp (3), when supporting segment (5), rests on a parallel plane with the skirt (2b) and separated from the skirt (2b) by a certain distance. Over the same end of the cylinder base or tube (1) to which piece (2) (equipped with ring holder) is found a piece (6), which is a rotatable impeller tip device, which the inventors refer to as a "Delhom apparatus," cylindrical in shape, and furnished with an impeller tip that is visible in the Figure and that has been indicated by reference number (7). This Delhom apparatus includes striations (7a) on its external perimeter surface, appearing longitudinally and distributed uniformly along its perimeter, envisaged generally for a better attachment of the piece during the manipulation of the introducer, extended to the total height of the piece except for two of the striations (7a) which are shorter and occupy positions diametrically opposed (from those that are visible in the Figure), and that serve to aid the positioning of a nerve (12) formed in the internal wall of the piece (11) used to protect the clamp once coupled to that end of the introducer assembly, when it is fully loaded. This clamp protector is configured as a shield, possessing an opening in its base (not visible in the figure), envisaged for the purpose of sterilization and bottom view, and also possesses a window (13) along its side wall that permits observation of the assembly when it is fully loaded.

Figure 5:
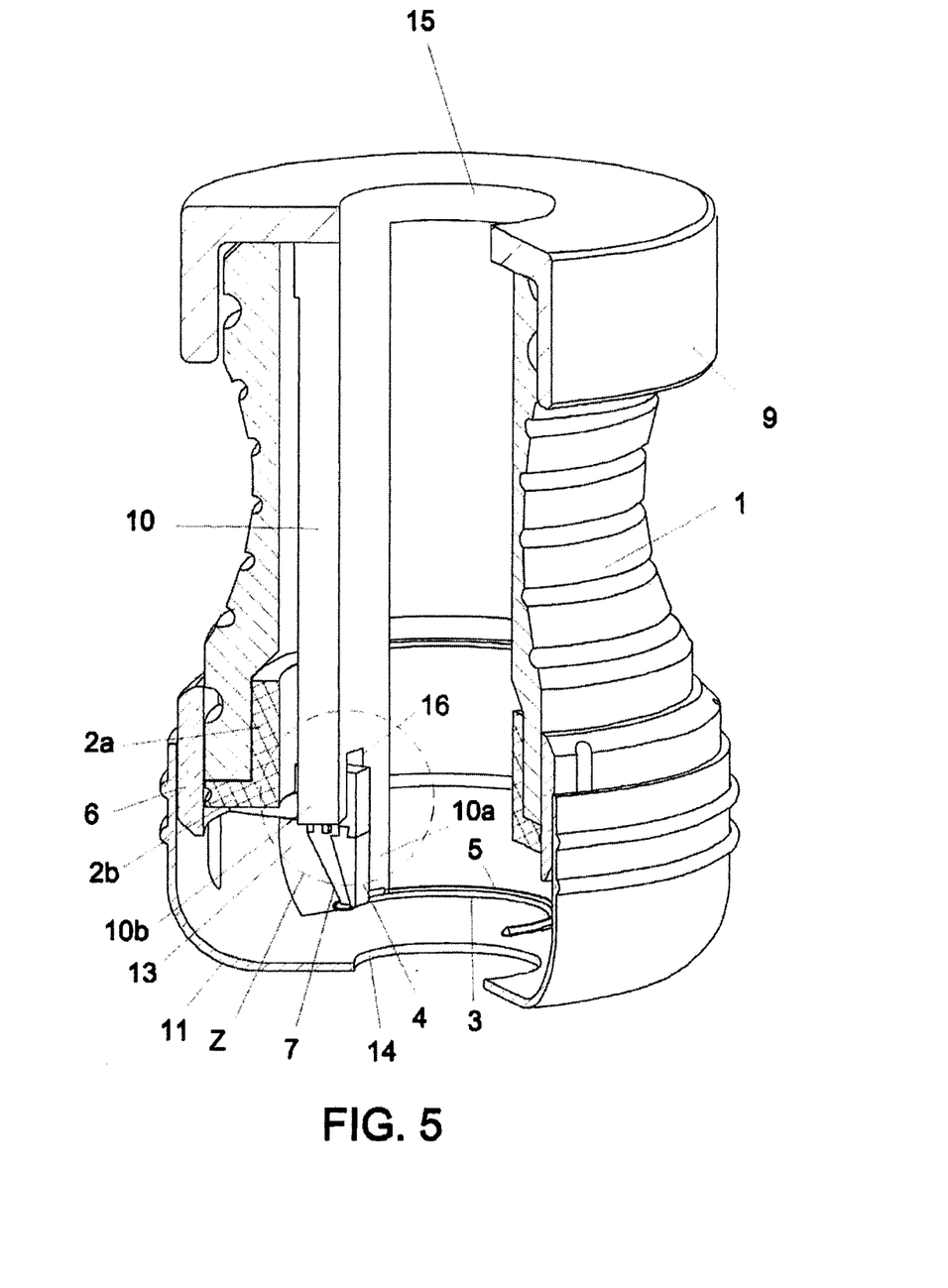
FIG. 5 shows the introducer completely loaded, with a section at a quarter so that one can appreciate the harmony among its diverse elements.

On the opposite end, the cylinder base (1) accepts the block cover (9), cylindrically shaped with an opening (15) centred on its base and envisaged for purposes of sterilization and for an upper view of the assembly from which a rod (10) extends longitudinally that runs along the inside of the cylinder base or tube (10, and which affords a recess or cavity on its free end (not visible in FIG. 1) that determines the formation of two walls (10a, 10b), one on each side of the recess, each being of different lengths and widths as can subsequently be seen in relation to the section of FIG. 5. Additionally, the end of this rod closes in a tip that is adapted to be inserted in an end-groove of the segment or ring, as one can also discern in relation to the same FIG. 5, see above.

Figure 2:
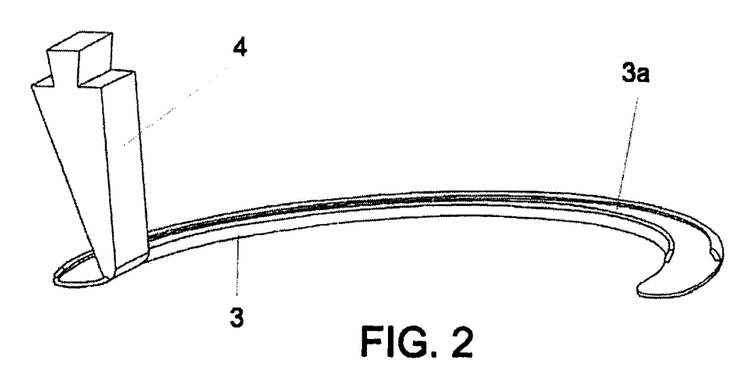
FIG. 2 schematic representation to scale and in perspective of the injector/clamp that is used to hold the intrastromal segment prior to insertion FIG. 3 schematic view in perspective of the cylinder base or introducing tube of the invention, illustrative of the means of coupling the end of the junction to the holding member of the ring holder.

In FIG. 2 is shown a schematic representation in perspective and to scale of the clamp (3) for supporting the segment or ring (5), and the linking arm (4) to piece (2) of the clamp (3), for purposes that can more clearly be seen in its constructive details. Only and exactly as it appears in the illustration, the clamp (3) is made in the shape of an arched track with a uniform curvature, in which the ring is to be pre-positioned, but still movable (not shown). The track (3a) of the clamp supports the segment or ring when it is placed on it, holding it securely to the interior surface thanks to the inward turning construction of its longitudinal borders as is shown. From this it can be discerned that the structural characteristics and dimensions of this clamp will vary according to the characteristics of the segments or rings to be inserted, and the positioning of the clamp will also be adjusted to the sense of insertion, either clockwise or counter-clockwise.

Figure 3:
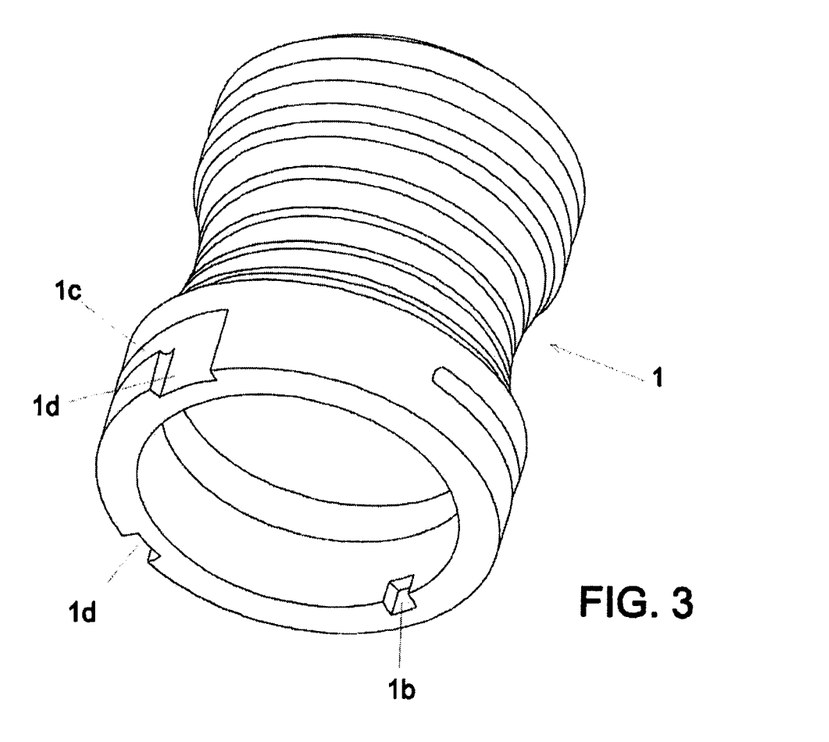

FIG. 3) shows the view in perspective of a cylinder-base or tunnel (1) constructed according to the invention design. This Figure permits one to see certain structural aspects of the cylinder base in greater detail, and in this sense one discerns that the it includes one or more recesses (1, 1b) sized in conformity with one or more of the hubs (2a) with which the cylindrical section (2c) of piece (2) is furnished extruding from the external surface over the perimeter skirt (2b). These features are included with a view to the coupling of the cylinder base to piece (2), the ring carrier.

In the same fashion, the body-base or tube (1) presents hollow grooving (1c) extending over the whole perimeter, that is parallel to, but a distance removed from, the perimeter border which is accessed by means of one or more of the recesses (1d), for purposes of coupling it to the Delhom apparatus (piece 6). This hollow grooving is intended to receive a hub (8) that arches toward the inside from the inside face of piece (6) of the Delhom apparatus, and is inserted onto the inside of the hollow grooving (1c) through the access recesses (1d).

Figure 4:
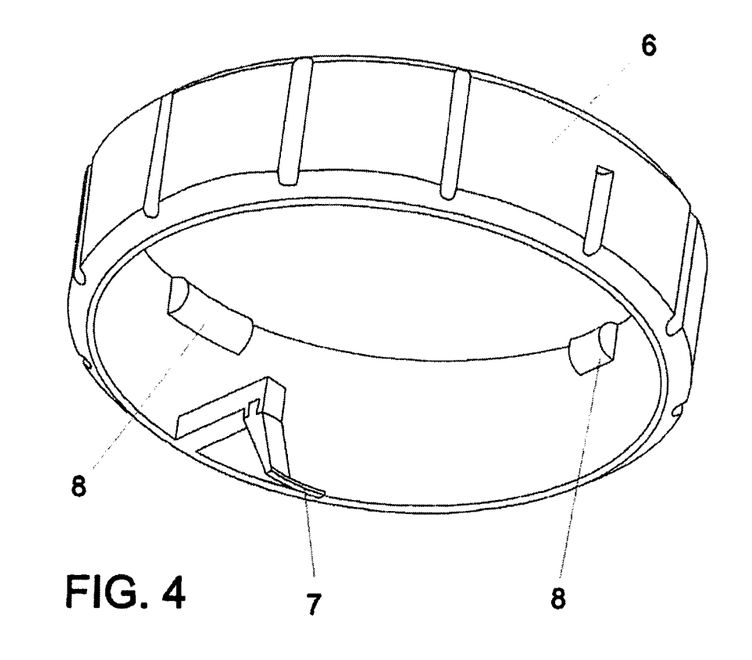
FIG. 4 schematic view in perspective from below, that shows the Delhom apparatus in greater detail.

FIG. 4 shows the Delhom apparatus (60 from a view in perspective taken from below to permit a greater understanding of the internal hubs (8) (in the embodiment described two hubs are envisaged (8), slightly differing in size, and separated by an angular distance equivalent to the separation between the access recesses (1d) of the cylinder base or tunnel 1. In the same way, one can also discern the position of the impeller tip (7) aimed at the central arm with the inside wall of the piece, projecting radially toward the inside with sufficient length to position the impeller tip (7) over the guide track (3a) of the clamp (3) that holds the segment or ring.

FIG. 5 shows the entire introducing assembly fully loaded, affording a one quarter view of the interior by virtue of the longitudinal section. The representation shows the opening (14) at the base of the protector clamp (11) in relation to one end of the inserting device, and also opening (15) in the form of a block cover (9) positioned in relation to the opposite end of the insertion device, both openings intended for purposes of sterilization and visualization of the interior as has been described in the preceding. In the same way, the assembly permits a view of a blocked zone enclosed by a circle marked with letter reference "z", in which a cavity (16) on the end of the rod (10) and delimited by walls (10a and 10b) intervenes with the carrier arm (4) of the clamp (3) and ring or segment positioned over it (ready for insertion) and the supporting member of the impeller tip (7) situated in the inside space of the cavity. At the same time, one can see that the delimiting wall (10b) of the cavity (16) is wider on one side and shorter than the other wall (10a) of the cavity (16) on the opposite side, such that the greatest wall width for wall (10b) is adequate to push both elements, the carrier arm (4) and impeller tip (7), with a turning movement that inserts the segment or ring (5) into the corneal tunnel. But when the assembly turns in the opposite direction, the lesser width of wall 10a across from the carrier arm (4), pushes the clamp (3) in the opposite direction (from the insertion sense) such that by manually holding down the Delhom apparatus along with the clamp together they form a ceiling for the segment or ring (5), allowing the clamp (3) to be retracted while holding the segment (5) ready to be inserted with no undesirable movement or loss of positioning. Once the operation is completed, the impeller tip (7) can also be retracted. With that, the implantation has been accomplished with no trauma, while the circular section of the assembly facilitates the manipulation and prevents movement of the patient's eye during surgery.

Figure 6:
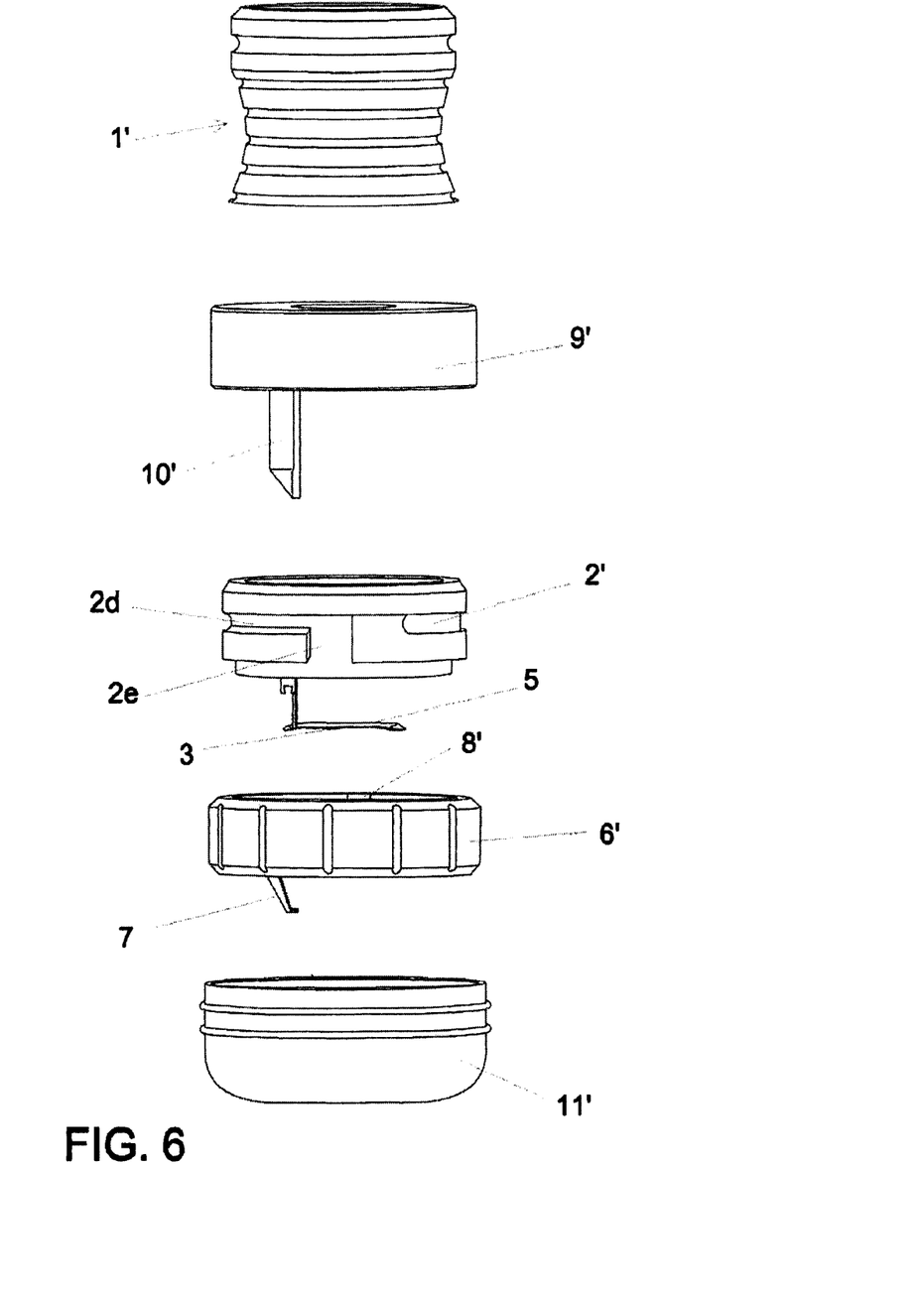
FIGS. 6 and 7 illustrate schematically the structural characteristics of the components of a modified version of the introducer of the present invention.

Finally, in relation to FIG. 6 of the drawings there is shown a modified version of the insertion device in which the body base or tunnel (1) is made with a titanium base and is recoverable for subsequent re-use in other surgical processes. The elements involved in this modified version are equivalent to those described for use in the first implementation, conforming approximately to the new form of presentation. Thus the principal piece (9) of the block cover shows a block rod (10') that is comparatively shorter than the block rod 10 in the first version, while piece (2') of the ring holder clamp consists of a cylinder shaped body, with hollow grooving (2d) on the outer surface of its perimeter wall extended over almost the whole perimeter, and furnished with recesses (2e) to access the hollow grooving that allow the passage of hubs (8) formed by the inside wall of the Delhom apparatus (6), for subsequent moveable prepositioning on the inside of the hollow grooving (2d). In the same way as the first embodiment, the ring holder (2') allows the support clamp (3) of the segment or ring (5) while piece (6) (the Delhom apparatus) is responsible for presenting the impeller tip (7). Also in the same manner as the first version described above, the inserting device includes a clamp protector coupling to the outside wall of the perimeter of the Delhom apparatus (6').

Figure 7:
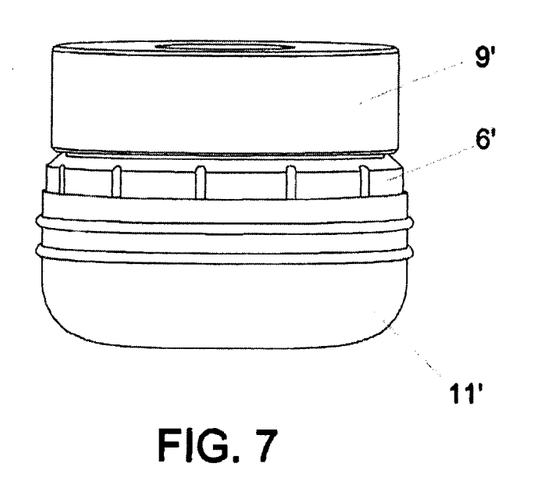

As we have just described, this alternative embodiment can be carried out exactly as it appears in FIG. 7 of the drawings, as part of a sterile set, while the cylinder base (1') is recoverable and re-usable and for that matter does not form part of the sterile assembly set. The distinct components appear coupled in the same way in which they will be subsequently used, with the ring-carrier (3) carrying the segment for insertion duly protected by the protector (11'), coupled to the end of the assembly, and with the cylinder base (1') sized adequately for coupling to the assembly in FIG. 7.

No further elaboration on the content of the present description is required for an expert in the subject to understand its extent and the advantages that it affords.

The preceding not withstanding and given that the description refers only to an example of one implementation of the invention, it will be understood that its essentials are capable of adapting to multiple variations in detail, that are equally safe, although they may affect such variables as the form, size or manufacturing materials of the assembly or of its parts, or of any other element do not affect the functioning of the invention delimited uniquely within the scope of the claims to follow.

The invention claimed is:

1. An implanting device for an intrastromal prosthesis that introduces, without forceps, a segment or ring onto an inside of an intrastromal tunnel made in a patient's cornea by a femtosecond laser technique, the implanting device comprising:
    a ring holder comprising a clamp configured to support the segment or ring to be inserted into the intrastomal tunnel;
    a cylinder base having a hollow cylindrical shape and first and second cylinder ends, wherein the first cylinder end is structured for attachment to the ring holder;
    a rotatable impeller tip device, comprising an impeller tip arm supporting an impeller tip, being joined to the first cylinder end and over the ring holder;
    a protective element arranged to protect the clamp that is positionable over the rotatable impeller tip device;
    a block cover, arranged on the second cylinder end; and
    a rod, which projects from the block cover and into the cylinder base to run along an inside wall of the cylinder base, having a free end with a recess that separates a first wall configured to concurrently move the clamp and the impeller tip arm in a first direction and a second wall configured to move the clamp relative to the impeller tip arm in a second direction opposite the first direction.

2. The implanting device as set forth in claim 1, wherein the ring holder comprises a cylindrical body portion sized for coupling onto the inside of the cylinder base, a perimeter skirt portion that extends around the cylindrical body portion, and one or more hubs that arch out from an outside wall surface of the cylindrical body portion, wherein the one or more hubs are sized for insertion into one or more recesses made in the inside wall of the cylinder base.

3. The implanting device as set forth in claim 2, wherein the cylinder base is disposable and an outside wall of the cylinder base is furnished with a plurality of perimeter grooves along a length of the outside wall and hollow grooving that is parallel to and removed a certain distance from the first cylinder end, the hollow grooving extending over nearly a whole perimeter of the cylinder base to communicate with access recesses made on the outside wall of the cylinder base that are sized to allow passage of the one or more hubs formed on an inside wall surface of the rotatable impeller tip device for providing quick-release positioning on an inside of the hollow grooving.

4. The implanting device as set forth in claim 1, wherein an inside of a perimeter wall of the protective element is provided with one or more ribs that are configured to engage with grooves formed on an outside perimeter wall of the rotatable impeller tip device, the ribs and grooves extending in a length direction of the cylinder base.

5. The implanting device as set forth in claim 4, wherein the protective element comprises a base with an opening configured for sterilization and visualization of an interior of the implanting device; and a side wall in which a window is provided for viewing the interior of the implanting device.

6. The implanting device as set forth in claim 1, wherein the block cover comprises a base with an opening configured for sterilization and viewing of the implanting device,
    wherein the recess of the rod is sized to accommodate a carrier arm configured to carry the impeller tip,
    wherein the first wall of the rod has a greater width than the second wall of the rod so that the first wall of the rod concurrently moves the clamp and the carrier arm in an inserting action of the segment or ring, which is arranged on the clamp, and the second wall of the rod has a width sized to only push the carrier arm to remove the clamp while the impeller tip holds the segment or ring in place in the intrastromal tunnel.

7. The implantation device as set forth in claim 1, wherein the rod has, on the free end, a finish shaped into a tip and sized for insertion into an inside of an end groove on an upper face of the segment or ring.

8. The implantation device as set forth in claim 1, wherein the cylinder base is recoverable and reusable and has a titanium base, wherein an outside wall of the cylinder base is furnished with hollow grooving that is parallel to and removed a certain distance from the first cylinder end, the hollow grooving extending over nearly a whole perimeter of the cylinder base to communicate with access recesses made on the outside wall of the cylinder base that are sized to allow passage of one or more hubs formed on an inside wall surface of the rotatable impeller tip device for providing quick-release positioning on an inside of the hollow grooving.

9. The implantation device as set forth in claim 1, wherein the ring holder, rotatable impeller tip device, protective element and block cover are recoverable to form a sterilized container.

* * * * *